United States Patent [19]
Bowen et al.

[11] Patent Number: 5,588,034
[45] Date of Patent: Dec. 24, 1996

[54] APPARATUS AND METHOD FOR INSPECTING A CRYSTAL

[75] Inventors: David K. Bowen; Charles R. Thomas, both of Warwickshire, England

[73] Assignees: Rolls-Royce PLC, London; University of Warwick, Coventry, both of England

[21] Appl. No.: 426,602

[22] Filed: Apr. 21, 1995

[30] Foreign Application Priority Data

Apr. 22, 1994 [GB] United Kingdom ............... 9408012

[51] Int. Cl.$^6$ ................................................. G01N 23/207
[52] U.S. Cl. ........................... 378/73; 378/70; 378/147
[58] Field of Search .......................... 378/70, 71, 72, 378/73, 74, 78, 79, 147, 149

[56] References Cited

U.S. PATENT DOCUMENTS 3,883,810  9/1974  Efanov et al. ........................ 378/149

Primary Examiner—Don Wong
Attorney, Agent, or Firm—Cushman Darby & Cushman IP Group of Pillsbury Madison & Sutro LLP

[57] ABSTRACT

An apparatus for inspecting single crystal specimens comprises an x-ray generator which supplies x-rays to a collimator. The collimator has a matrix of apertures to produce a plurality of parallel x-ray beams which are directed onto a surface of the specimen. An x-ray detector detects the x-ray beams diffracted from the surface of the specimen, corresponding to each of the parallel x-ray beams. At each symmetry pole of an overall Laue pattern an accurately predictable pattern of spots is produced on the x-ray detector, if the orientation and shape of the specimen crystal is known. Each spot corresponds to where one of the diffracted beams strikes the detector. A disarrangement of one or more of the spots indicates a difference in crystal orientation.

23 Claims, 4 Drawing Sheets

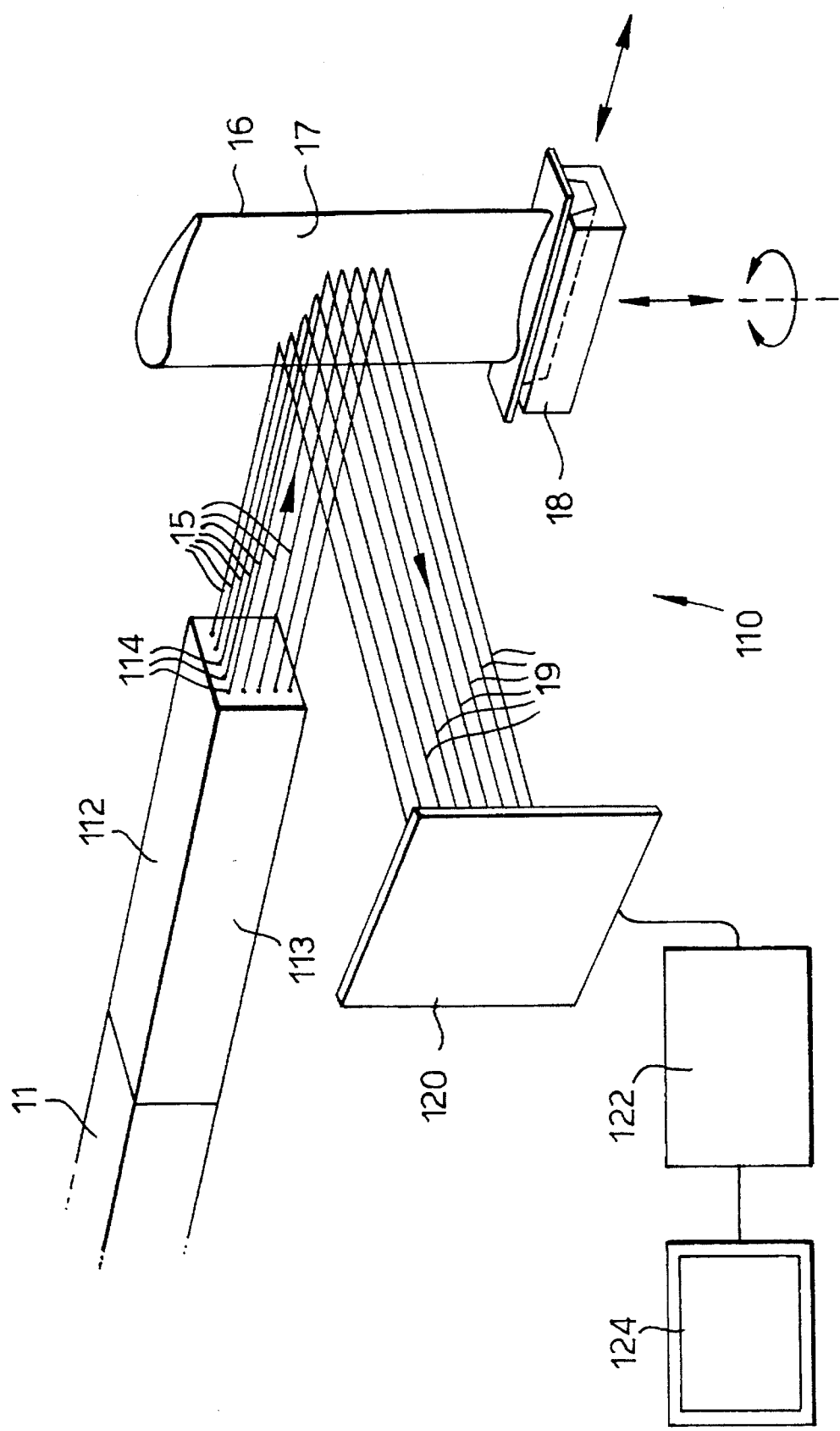

APPARATUS AND METHOD FOR INSPECTING A CRYSTAL

FIELD OF THE INVENTION

The present invention relates to an apparatus and a method for inspecting a crystal. It is particularly useful in the inspection of a single crystal object such, for instance, as a cast single crystal component for a gas turbine engine, but it is applicable also to other objects and to a single crystal forming part only of a complete object.

BACKGROUND OF THE INVENTION

Cast single crystal components may suffer from surface breaking secondary grains, or defects. These surface breaking secondary grains, or defects have a minimum size of the order of 0.008 inch diameter (0.20 mm). At present there is no known apparatus or method which is capable of rapidly detecting and characterising these surface breaking secondary grains, or defects, in cast single crystal components, so that it may be incorporated as a step in the manufacturing process for the production of cast single crystal components. Cast single crystal components may suffer from surface breaking secondary grains, or defects, such as secondary grain boundaries, slivers, equiaxed grains, freckles, recrystallised grains, secondary grains, zebra grains and striations, which all differ in surface dimensions and crystal orientation relative to the main single crystal.

SUMMARY OF THE INVENTION

The present invention seeks to provide an apparatus and a method for inspecting a crystal which is capable of rapidly detecting all surface breaking secondary grains or defects.

Accordingly the present invention provides an apparatus for inspecting a crystal comprising a specimen holder arranged to hold the crystal, means to direct a plurality of parallel X-ray beams on to a surface of the crystal and X-ray detector means arranged to detect the X-rays diffracted by the surface layers of the crystal to detect defects in the crystal.

Preferably the means to direct a plurality of parallel X-ray beams on to the surface of the crystal comprises an X-ray generator arranged to produce a beam of X-rays and to direct the beam of X-rays into a collimator, the collimator being arranged to produce a plurality of parallel collimated X-ray beams and to direct the plurality of X-ray beams on to the surface of the crystal.

Preferably the collimator comprises an X-ray opaque member having a plurality of holes extending therethrough.

The holes in the X-ray opaque member may be arranged in any suitable one dimensional, or two dimensional matrix.

Preferably the diameter of each parallel collimated X-ray beam is of the order of the minimum detectable defect size.

Preferably the diameter is equal to or less than 0.2 mm, and preferably is 0.1 mm.

Preferably the spacing between the parallel X-ray beams is equal to or less than 2 mm.

Preferably the angular divergence of each incident X-ray beam is equal to or less than 1.0°.

Preferably the angle between the parallel X-rays beams directed onto the surface of the crystal and the X-rays reflected by the surface layers of the crystal is less than 90°.

Preferably the X-ray detector means comprises a real time detector. The X-ray detector means may comprise a photographic film.

Preferably the specimen holder and specimen and the means to direct the plurality of parallel X-ray beams onto the surface of the crystal are relatively movable to allow the whole of the surface of the specimen to be examined.

Preferably the specimen holder is movable.

Preferably the crystal is a single crystal turbine blade or vane.

Preferably the X-ray detector means comprises a first and second detector arranged at a predetermined angle relative to each other.

Preferably both detectors are in a plane normal to the diffracted X-ray beams.

Preferably the predetermined angle is the angle between two <210> single crystal directions.

The present invention also provides a method of inspecting a crystal comprising directing a plurality of parallel X-rays beams on to a surface of a crystal, detecting the X-rays diffracted by the surface layers of the crystal to detect defects in the crystal and scanning the plurality of parallel X-ray beams over the whole of the surface of the crystal.

BRIEF DESCRIPTION OF THE DRAWINGS

The present invention will be more fully described by way of example, with reference to the accompanying drawings in which:

FIG. 3 is a diagram of layout of an alternative apparatus for inspecting a crystal according to the present invention.

DETAILED DESCRIPTION OF THE INVENTION

Figure 1:
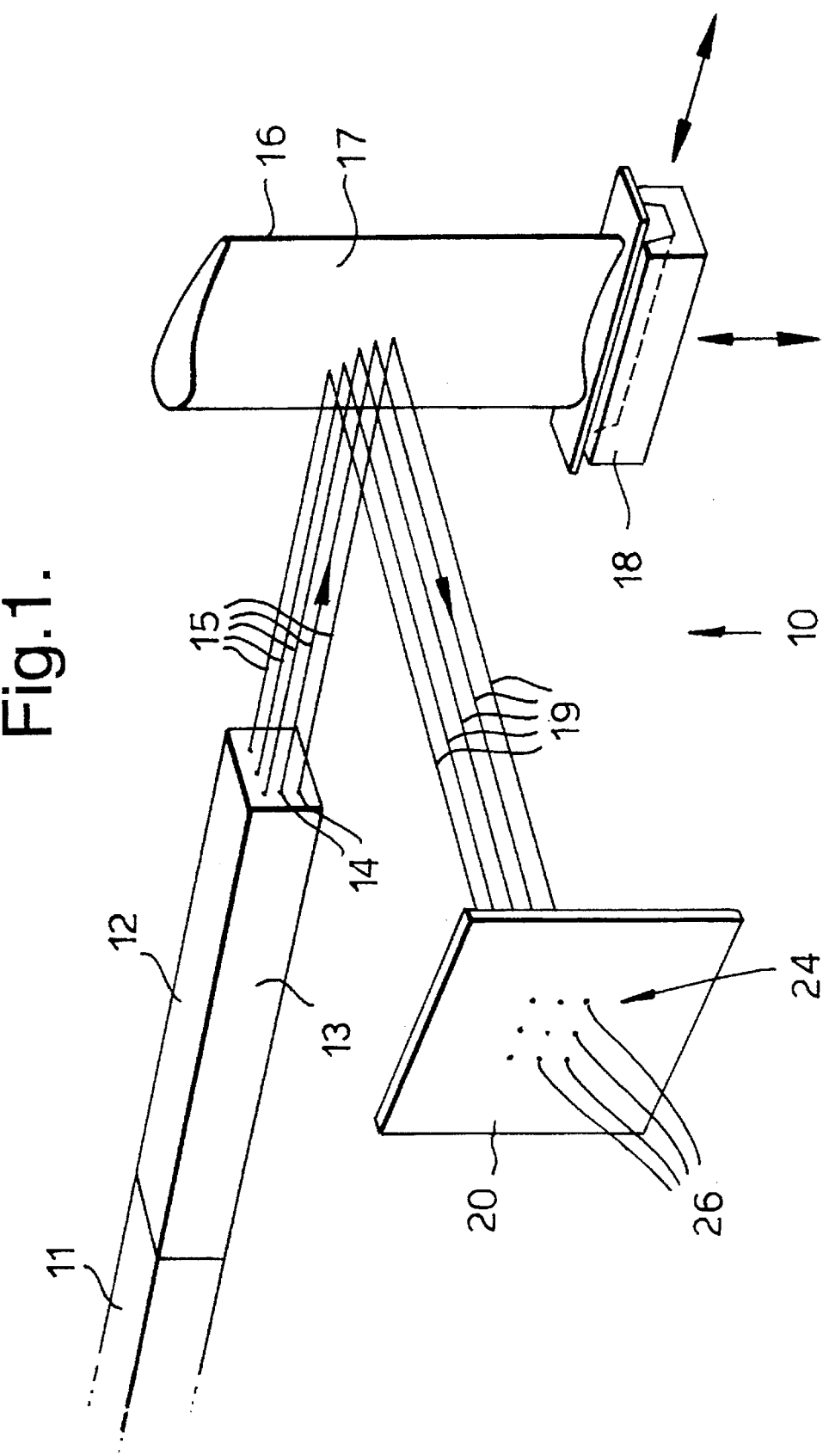
FIG. 1 is a diagram of the layout of an apparatus for inspecting a crystal according to the present invention.

An apparatus 10 for inspecting a crystal is shown in FIG. 1 and comprises an X-ray generator 11 which produces polychromatic, white, radiation suitable for use in the Laue method. The X-ray generator 11 includes an X-ray tube which produces X-rays with wavelengths between 0.04 to 0.25 nm. These X-rays pass to a collimator 12 which comprises an X-ray opaque member 13. The member 13 has a plurality of parallel sided holes 14 extending therethrough. The X-rays emerge from the collimator 12 as a plurality of parallel collimated beams 15. In this example the X-ray generator 11 is a source of divergent X-rays, and as a result each individual beam 15 is divergent, but the mean beam path for each individual X-ray beam 15 is parallel to the mean beam path of all the other beams 15. The collimator 12 directs the parallel beams 15 onto a surface 17 of a specimen 16 which is held in a specimen holder 18. In this instance the specimen 16 comprises a turbine blade for a gas turbine engine, and is cast as a single crystal which makes up the complete blade. It is desirable that this crystal should have the same orientation throughout the longitudinal extent of the blade and at all points on the blade surface. The apparatus of the invention is used to rapidly analyse the surface of the blade to detect surface breaking secondary grains, or defects, and hence measure the differences in crystal orientation.

The specimen 16 is easily held in the specimen holder 18 because the blade has a root portion which can be securely gripped by the specimen holder 18. Alternatively the shroud/tip of the blade may be held in the specimen holder to allow the root of the blade to be inspected. The specimen holder 18 and specimen 16 are movable relative to the collimator 14 so that the parallel beams 15 are capable of scanning the whole surface 17 of the specimen 16, or a portion for which it is important to know that secondary grain defects, or differences in crystal orientation, do not occur.

Each of the diverging and parallel X-ray beams 15 strikes the surface 17 of the specimen 16 and is diffracted from the surface 17 of the specimen 16 to produce its own Laue pattern. Due to the fact that a plurality of X-ray beams 15 are arranged side by side in any suitable one dimensional, or two dimensional, matrix a number of diffracted beams 19 are found at each symmetry pole 24 of an overall Laue pattern 22. Thus a number of spots 26, corresponding to the diffracted beams 19, are found at each symmetry pole 24 of the overall Laue pattern 22. A photographic film 20 is used to detect the diffracted beams 19 at one symmetry pole 24.

If the orientation of the single crystal and the shape of the specimen are known, an accurately predictable pattern of spots 26 is produced at the symmetry pole 24, which is observed on the film 20. Each spot 26 corresponds to where one of the diffracted beams 19 strikes the film 20. A disarrangement of the pattern of spots 26 indicates a difference in crystal orientation, or surface breaking secondary grains, or defects. Different disarrangements of the pattern indicate different types of crystal orientation.

Figure 2:
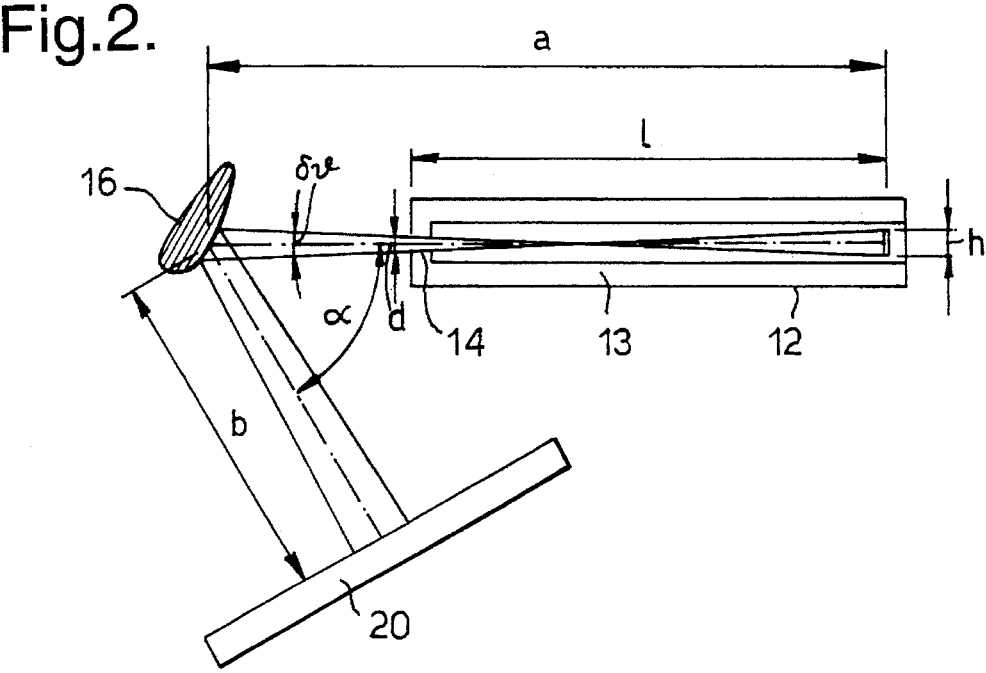
FIG. 2 is a diagram illustrating the X-ray optics of an individual X-ray beam.

The X-ray optics of the apparatus are shown in FIG. 2. The source to specimen distance is indicated by a, the collimator length is indicated by 1, the source height is indicated by h, the collimator aperture diameter for each beam is indicated by d, the specimen to film distance is indicated by b, the beam divergence is indicated by $\delta\theta$ and the inclination of the diffracted beam to the incident beam is indicated by $\alpha$.

$$\delta\theta = (h+d)/l$$

The medium intensity region, excluding the penumbra, beam size on the specimen has a diameter D $$D = da/l$$

The film is orientated perpendicularly to the diffracted beams, this results in minimum distortion of the images and gives the most straightforward interpretation. The angle of inclination $\alpha$, may be taken as any angle between 0° or 90°.

In the apparatus shown in FIG. 1, the collimator 12 produces nine parallel beams 15 arranged in a three by three array. The parallel beams 15 are separated by 1 mm, and d=0.1 mm, l=150 mm, a=200 mm, h=0.4 mm to produce parallel beams each of which have a beam diameter D on the specimen of 0.15 mm with a divergence of 0.2° and b=30 mm. Variation in these parameters may be used to alter the beam divergence and beam diameter on the surface of the specimen.

An alternative apparatus 110 for inspecting a crystal is shown in FIG. 3, and is substantially the same as that shown in FIG. 1, and like parts are indicated by like numerals. The apparatus 110 in FIG. 3 differs primarily from that in FIG. 1 in that a real time detector 120 is used to detect the X-ray beams 19 diffracted from the surface 17 of the specimen 16 and the collimator 112 produces twenty five diverging and parallel beams 15 arranged in a five by five array. The real time detector 120 with linear resolution of 20 µm to 30 µm converts the X-ray signal to an electrical signal suitable for a video. The electrical signals, corresponding to the TV image, produced by the image converter are digitised and several images are integrated to remove the effect of noise. A processor 122 analyses the TV image using image processing to identify appropriate patterns to give an indication of correct orientation of the crystal or a different orientation. The TV image may also be displayed on a TV monitor 124.

Figure 4:
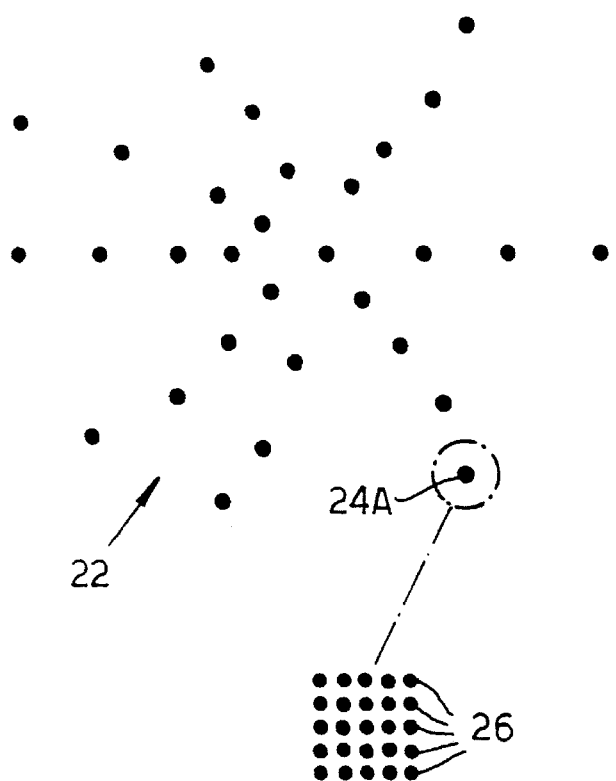
FIG. 4 is a diagram representing an overall multiple Laue pattern.
Figure 5:
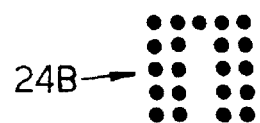
FIG. 5 is a diagram representing an individual symmetry pole within a Laue pattern for one type of crystal defect.
Figure 6:
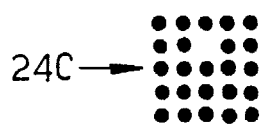
FIG. 6 is a diagram representing an individual symmetry pole within a Laue pattern for a second type of defect.
Figure 7:
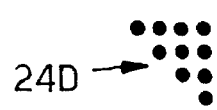
FIG. 7 is a diagram representing an individual symmetry pole within a Laue pattern for a third type of defect.

As discussed previously, any disarrangement of the pattern of spots 26 in the symmetry pole 24 indicates a difference in crystal orientation. FIG. 4 shows that from each overall Laue pattern 22, from a given (h,k,1) plane only a single symmetry pole 24A need be observed. Each symmetry pole 24A of the overall Laue pattern 22 comprises twenty five spots 26, in this example, and this figure corresponds to a region where the crystal has the same orientation. In FIG. 5 the symmetry pole 24B of the overall Laue pattern 22 has four spots 26 in a line displaced. This corresponds to a region in the crystal where there is a sliver type crystal misorientation. In FIG. 6, the symmetry pole 24C of the overall Laue pattern 22 has a single spot 26 displaced. This corresponds to a freckle type crystal misorientation. In FIG. 7, the symmetry pole 24D of the overall Laue pattern 22 has a diagonal half of the pattern displaced. This corresponds to a bicrystal type misorientation.

It has been found that 40 video frames are required to acquire an image with a sealed X-ray tube generator running at 45 KV to 70 KV and 40 mA to 70 mA and with a beam divergence of 1°. It is preferred that a rotating anode X-ray generator is used because these devices are available at powers of 50 KW to 80 KW and these allow the acquisition of images with a beam divergence of 1° with 2 to 4 frames of 160 ms.

The time taken to scan the whole of surface of the specimen varies inversely with the number of parallel beams in the array and with the inverse square of the spatial resolution. For example reducing the spatial resolution from 0.2 mm to 0.5 mm and increasing the number of parallel beams from 9 to 20 generates a reduction in the scan time by a factor of 3.5.

It may be suitable in some circumstances to use a one dimensional array of diverging and parallel beams rather than a two dimensional array of diverging and parallel beams.

Figure 8:
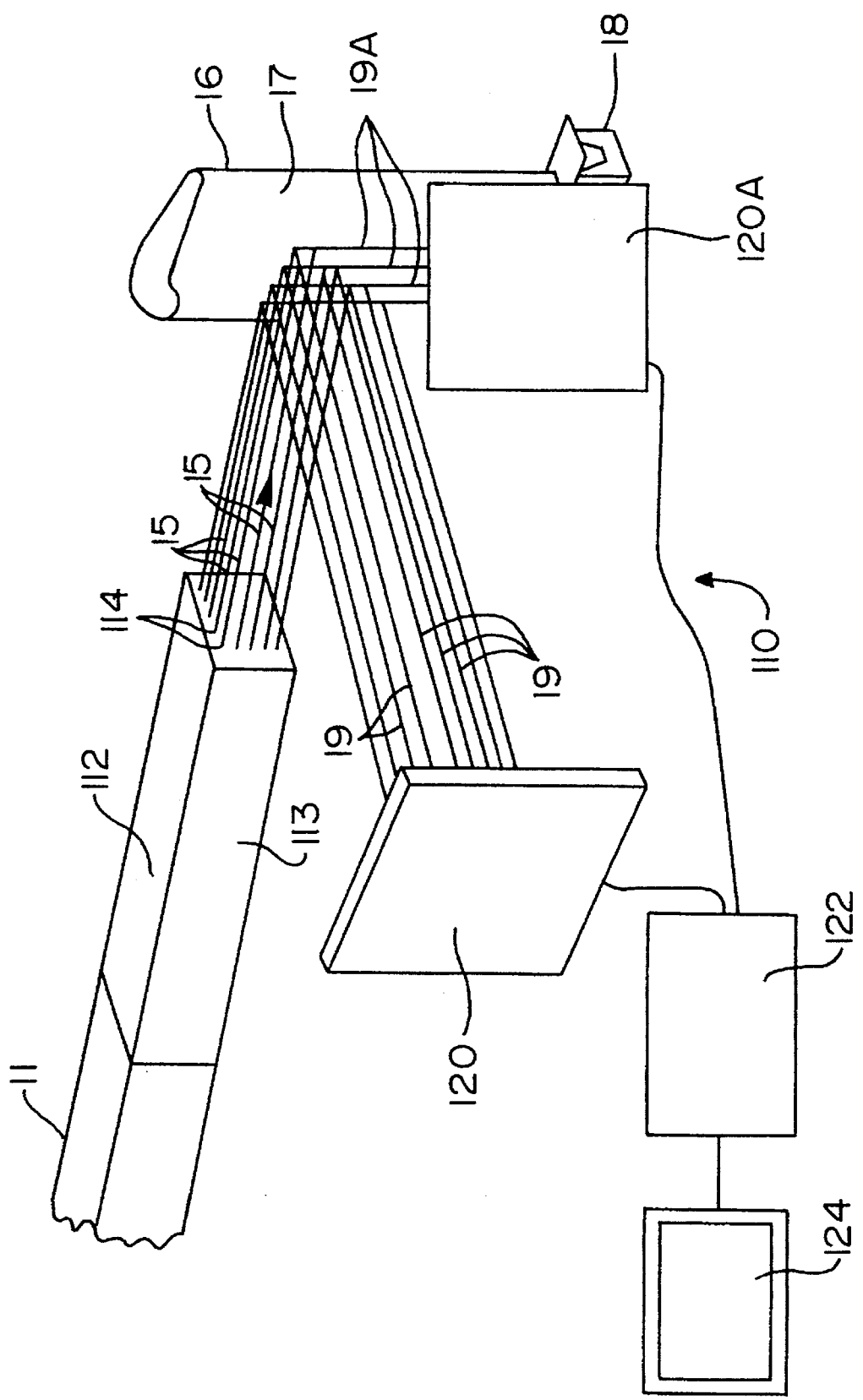
FIG. 8 is a view similar to FIG. 3 but showing a second detector in place at an angle relative to the first detector.

There is an ambiguity in the orientation determination if the misorientation is closely similar to a rotation about the [210] axis that is also the diffracted beam vector. The Laue spot is invariant to this rotation. In order to resolve the ambiguity a second [210] diffraction symmetry pole is used. In a first method of resolving the ambiguity the detector is moved about any axis, which is not the diffraction beam vector, to detect the second [210] diffraction symmetry pole using the same detector. In a second method of resolving the ambiguity the specimen is rotated about any axis, which is not the diffraction beam vector, to detect the second [210] diffraction symmetry pole using the same detector. Alternatively, as shown in FIG. 8, in a third method of resolving the ambiguity a second fixed detector is arranged at the appropriate angle relative to the first fixed detector to detect the other [210] diffraction symmetry pole. The third alternative increases the cost but does not increase the time. The detection surfaces of both the detectors are arranged in a plane normal to the diffracted X-ray beams, fixed at a relative angle of 36.87°, the angle between two [210] directions.

The surface orientation varies with respect to the crystal plane orientation all over a turbine blade. This has the effect of expanding or compressing the array of parallel beams. In order to maintain the spatial resolution and to minimise distortion of the array of parallel beams it may be necessary to use different <210> reflections at different point of the turbine blade.

Preferably the spacing between neighbouring collimated X-ray beams is of the order of the minimum prescribed detection size of a single crystal defect. However, as long as the X-ray beams do not overlap there is no limitation.

Although the description has referred to the use of two dimensional matrices, or grids, of X-ray beams using nine and twenty five beams, it is clearly possible to use two dimensional matrices, or grids, of X-ray beams with any other suitable number of X-ray beams. Similarly it may be desirable to use one dimensional matrices, or arrays, of X-ray beams of any suitable number. The matrices, or grids, may include cross-shapes or any other suitable pattern of X-ray beams.

We claim:

1. An apparatus for detecting defects in a crystal comprising a specimen holder arranged to hold a crystal, a polychromatic x-ray generator arranged to produce a beam of polychromatic x-rays, a collimator arranged to receive the beam of polychromatic x-rays from the polychromatic x-ray generator, the collimator having means to produce a plurality of separate parallel polychromatic x-ray beams in a predetermined pattern and to direct the plurality of separate parallel polychromatic x-ray beams in the predetermined pattern onto the surface layers of the crystal, an x-ray detector arranged to detect at least one separate diffracted x-ray beam diffracted by the surface layers of the crystal, each of the separate diffracted x-ray beams corresponding to a respective one of the plurality of separate parallel polychromatic x-ray beams directed onto the surface layers of the crystal, the x-ray detector determining whether any of the separate diffracted x-ray beams have been displaced from the predetermined pattern to indicate that there is a defect in the surface layers of the crystal.

2. An apparatus for detecting defects in a crystal comprising a specimen holder arranged to hold a crystal, a polychromatic x-ray generator arranged to produce a beam of polychromatic x-rays, a collimator arranged to receive the beam of polychromatic x-rays from the polychromatic x-ray generator, the collimator having means to produce a plurality of separate parallel polychromatic x-ray beams in a predetermined pattern and to direct the plurality of separate parallel polychromatic x-ray beams in the predetermined pattern onto the surface layers of the crystal, the collimator comprising an x-ray opaque member which has a plurality of parallel apertures extending therethrough to produce the plurality of separate parallel polychromatic x-ray beams, the dimensions of each aperture are arranged to produce a beam diameter on the surface layers of the crystal of the order of the minimum detectable defect size, the apertures are spaced apart in the x-ray opaque member to produce spacings between the separate parallel polychromatic x-ray beams on the surface layers of the crystal of the order of the minimum detectable defect size, an x-ray detector arranged to detect at least one separate diffracted x-ray beam diffracted by the surface layers of the crystal, each of the separate diffracted x-ray beams corresponding to a respective one of the plurality of separate parallel polychromatic x-ray beams directed onto the surface layers of the crystal, the x-ray detector determining whether any of the separate diffracted x-ray beams have been displaced from the predetermined pattern to indicate that there is a defect in the surface layers of the crystal.

3. An apparatus as claimed in claim 1 in which the collimator comprises an x-ray opaque member having a plurality of apertures extending therethrough.

4. An apparatus as claimed in claim 3 in which the apertures in the x-ray opaque member are arranged in a one dimensional matrix.

5. An apparatus as claimed in claim 3 in which the apertures in the x-ray opaque member are arranged in a two dimensional matrix.

6. An apparatus as claimed in claim 3 in which the dimensions of each aperture are arranged to produce a beam diameter on the surface layers of the crystal of the order of the minimum detectable defect size.

7. An apparatus as claimed in claim 2 or claim 6 in which each aperture has a diameter of between 0.1 mm and 0.5° mm.

8. An apparatus as claimed in claim 7 in which the diameter is 0.2 mm.

9. An apparatus as claimed in claim in which the diameter is 0.1 mm.

10. An apparatus as claimed in claim 3 in which the apertures are spaced apart in the x-ray opaque member to produce spacings between the separate parallel polychromatic x-ray beams on the surface layers of the crystal of the order of the minimum detectable defect size.

11. An apparatus as claimed in claim 2 or claim 10 in which the apertures are spaced apart by 2 mm.

12. An apparatus as claimed in claim 2 or claim 10 in which the apertures are spaced apart by 1 mm.

13. An apparatus as claimed in claim 1 or claim 2 in which the angle between the separate parallel polychromatic x-ray beams directed onto the surface of the crystal and the x-ray beams diffracted by the surface layers of the crystal is less than 90°.

14. An apparatus as claimed in claim 1 in which the x-ray detector means comprises a photographic film.

15. An apparatus as claimed in claim 1 in which the x-ray detector means comprises a real time detector.

16. An apparatus as claimed in claim 1 in which the specimen holder and crystal and the polychromatic x-ray generator and collimator are relatively movable to allow the whole of the surface of the crystal to be examined.

17. An apparatus as claimed in claim 16 in which the specimen holder and crystal are movable.

18. An apparatus as claimed in claim 1 in which the crystal is selected from the group comprising a single crystal turbine blade and a single crystal turbine vane.

19. An apparatus for detecting defects in a crystal comprising a specimen holder arranged to hold a crystal, a polychromatic x-ray generator arranged to produce a beam of polychromatic x-rays, a collimator arranged to receive the beam of polychromatic x-rays from the polychromatic x-ray generator, the collimator being arranged to produce a plurality of separate parallel x-ray beams in a predetermined pattern and to direct the plurality of separate parallel polychromatic x-ray beams in the predetermined pattern onto the surface layers of the crystal, an x-ray detector arranged to detect at least one separate diffracted x-ray beam diffracted by the surface layers of the crystal, each of the separate diffracted x-ray beams corresponding to a respective one of the plurality of separate parallel polychromatic x-ray beams directed onto the surface layers of the crystal, the x-ray detector determining whether any of the separate diffracted x-ray beams have been displaced from the predetermined pattern to indicate that there is a defect in the surface layers of the crystal, said x-ray detector means comprising a first detector and second detector, said first detector and second detector being arranged in a predetermined angle relative to each other.

20. An apparatus as claimed in claim 19 in which the first detector and the second detector are arranged in a plane normal to the diffracted x-ray beams.

21. An apparatus as claimed in claim 20 in which the predetermined angle is the angle between two <210> single crystal directions.

22. A method of detecting defects in a crystal comprising (a) producing a plurality of separate parallel polychromatic x-ray beams in a predetermined pattern, (b) directing the plurality of separate parallel polychromatic x-ray beams in the predetermined pattern onto the surface layers of a crystal to be inspected, (c) detecting at least one separate diffracted x-ray beam diffracted by the surface layers of the crystal, each of the separate diffracted x-ray beams corresponding to a respective one of the plurality of separate parallel polychromatic x-ray beams directed onto the surface layers of the crystal, (d) determining whether any of the separate diffracted x-ray beams diffracted by the surface layers of the crystal have been displaced from the predetermined pattern to indicate that there is a defect in the surface layers of the crystal.

23. A method as claimed in claim 22 comprising scanning the plurality of separate parallel polychromatic x-ray beams in the predetermined pattern over the whole of the surface of the crystal.

* * * * *